US005449601A

United States Patent [19]

Jean et al.

[11] Patent Number: 5,449,601

[45] Date of Patent: Sep. 12, 1995

[54] PROCESS FOR THE IDENTIFICATION OR DETERMINATION OF PROTEINS AND ITS APPLICATIONS

[75] Inventors: Fréderic Jean; Jacques Barbet; Michel Delaage, all of Boûches-du-Rhône, France

[73] Assignee: Immunotech, Marseilles, France

[21] Appl. No.: 61,350

[22] Filed: May 17, 1993

Related U.S. Application Data

[63] Continuation of Ser. No. 680,882, Apr. 5, 1991.

[30] Foreign Application Priority Data

Apr. 6, 1990 [FR] France ................................ 90 04774

[51] Int. Cl.[6] ................................................ C12Q 1/70

[52] U.S. Cl. ......................................... 435/5; 435/7.1; 435/974; 436/174; 436/175; 530/324; 530/325; 530/326; 530/327; 530/328; 530/329

[58] Field of Search ............................ 435/5, 7.1, 974; 436/174, 175; 530/324–329

[56] References Cited

U.S. PATENT DOCUMENTS 4,658,022 4/1987 Knowles et al. .................... 530/402

OTHER PUBLICATIONS

Biotech Research Laboratories Inc.: Immunological Kit for HTLV-III p. 24 Detection 1986.

Modrow et al: Carrier Bound Synthetic . . . HIV-2 Infection J. of AIDS vol. 2, #2, pp. 141–148 1989.

Rückert et al: Some Methodic Aspects . . . of $\beta$-Endorphin Exp Clin. Endocrinol v87, #3, 1986 pp. 277–287.

*Primary Examiner*—Christine M. Nucker

*Assistant Examiner*—Jeffrey Stucker

*Attorney, Agent, or Firm*—Browdy and Neimark

[57] ABSTRACT

Process for the identification or determination of proteins by producing antibodies with the aid of peptides that are made immunogenic if necessary, and then using the resulting antibodies to determine the proteins of interest, starting with a sample that contains these and which is treated to liberate the said peptides, in which process the said peptide is so chosen that it matches a known amino acid sequence of the said protein and is used as a protein fragment that the protein can be made to release on enzymatic treatment, after which it is synthesized, the invention also relating to the applications of this process for the identification or the determination of proteins.

23 Claims, 1 Drawing Sheet

PROCESS FOR THE IDENTIFICATION OR DETERMINATION OF PROTEINS AND ITS APPLICATIONS

This application is a continuation of application Ser. No. 07/680,882, filed Apr. 5, 1991.

FIELD OF THE INVENTION

The present invention relates to a process for the identification or determination of proteins, as well as to the applications of this process.

BACKGROUND OF THE INVENTION

The accurate immunological determination of proteins calls for antibodies that have a sufficiently high affinity to these proteins to allow them to be detected in the small amounts in which they are generally encountered. Furthermore, these antibodies must also be sufficiently specific to rule out any interference by other constituents of the medium in which the determination is carried out. However, such antibodies are often unavailable, because it is difficult to obtain a sufficiently large and suitably pure source of the antigen in question.

However, the use of synthetic peptides as immunogens has made it possible to obtain antibodies to antigens that are rare, to antigens of which only the amino acid sequence is known, and to certain weakly immunogenic epitopes located in a protein molecule. In most cases, however, the resulting antibodies to such synthetic peptides do not recognize the whole protein with a sufficient avidity to permit an immunoassay having the required sensitivity to be based on them.

Numerous attempts have been made to eliminate interference by the other constituents of the medium in which the protein immunoassay is conducted. In one of these methods, described in European Patent Application No. 51,985, the determination is carried out after the sample has been treated with a proteolytic agent. The way it is described there, this method permits the selective destruction of the epitopes on the contaminating proteins while leaving intact the epitopes on the protein to be determined, also permitting the determination of the protein fragments that carry specific epitopes and which are obtained by proteolytic cleavage. This is achieved there with the aid of antibodies obtained by immunizing animals with purified fragments obtained by cleaving the said protein.

However, both the techniques proposed in the publication mentioned above have some drawbacks. In the first technique outlined above, the selective destruction of the epitopes on the interfering protein molecules can only be accomplished if one knows exactly both a) the location of the epitopes that are recognized by the antibodies involved in the determination and b) the nature of the contaminating proteins, or if one carries out an extensive study of the different techniques of proteolytic fragmentation.

In the second technique outlined above, the determination of the proteolytically obtained fragments with the aid of antibodies obtained by immunization with purified fragments necessitates a large amount of very pure native protein. Furthermore, the detection of specific antibodies calls for the characterization of the proteolytically obtained purified fragments prior to their use as immunogens, or for a thorough investigation of the specificity of the antibodies obtained after immunization with the different peptides.

A method has also been described for the determination of the precursor of vasopressin by means of antibodies to vasopressin itself. In this method, the antigenic determinant is reconstituted prior to the determination, by means of an enzymatic and chemical treatment [see A. Cupo, G. Rougon-Rapuzzi and M. Delaage: "Immunochemical detection of vasopressin precursors: artificial processing and quantitation along the hypothalamo-hypophyseal axis", *Eur. J. Biochem.*, 115 (1981) pp. 169–174].

A similar method has been used successfully to determine met-enkephalin by employing antibodies raised to a natural fragment of its precursor. This determination is carried out after treating the sample first with trichloroacetic acid in order to eliminate the natural fragment and then with trypsin [see A. Cupo, P. A. Pontarotti, T. Jarry and M. A. Delaage: "A new immunological approach to the detection and quantitation of met-enkephalin precursors in the rat brain", *Neuropeptides,* 4 (1984) pp. 375–387].

SUMMARY OF THE INVENTION

In the present invention, a study of the primary structure of the protein to be determined permits a simpler direct determination of specific proteolytically obtained fragments, without either prior treatment or subsequent modification. This method differs from the previous ones mentioned above in three essential respects:

1) the immunizing peptide is an artificial fragment,
2) no extraction is carried out to eliminate a natural fragment, and
3) no chemical modification needs to be effected on the samples.

The aim of the present invention is therefore to provide a process for the identification or determination of proteins, in which process the antibodies are produced with the aid of a peptide that is made immunogenic if necessary, then the resulting antibodies are used to determine the protein of interest, and in which process one starts with a sample that contains this protein and is treated to make it release the said peptide, characterized in that the said peptide is chosen from a known sequence of the said protein and is used as a fragment (or part of a fragment) of the protein that the latter can liberate on enzymatic treatment, after which the peptide is synthesized.

Such a process has the advantages that the use of synthetic peptide-type immunogens offers, namely easy preparation and choice of the epitope of interest. It also makes it possible to avoid the problems caused by the affinity losses that occur in the immunoassay of a native protein. This is possible here because the immunogen matches perfectly the antigen to be determined, for it can be e.g. completely identical to it. Moreover, there are numerous techniques available to the expert for effecting the cleavage of the protein with the aid of proteolytic enzymes that ensure bond scission at specific sites that are easy to identify in the primary structure of the protein, and this range of techniques offers a wide choice of peptide fragments for use.

The preparation of antibodies with the aid of peptides is well known from the prior art. If the peptides are not immunogenic or not sufficiently so, they can be made that e.g. by binding them on a macromolecule, notably of protein origin.

The peptides can be chosen from a known sequence of amino acids or deduced from the sequence of nucleic acids in the corresponding gene. The peptides are so chosen that they match a fragment of a protein such as a hormone or a viral protein.

The peptides selected are in fact chosen because they correspond to proteic fragments obtainable by an enzymatic treatment. They are exemplified by the "trypsin fragments" obtained by treating the protein in question with trypsin.

The term "part of a fragment" mentioned above denotes a C-terminal, N-terminal or non-terminal part of the protein fragment. In the following description, the word "fragment" will be used to mean both a fragment and part of a fragment.

It is of course also possible to treat the starting protein with other single enzymes, or with a set of enzymes, such as the trypsin—chymotrypsin—proline endopeptidase set.

The peptides are also chosen according to their size and according to how representative they are of either a given single protein or of a group or "family" of proteins.

One or more peptides (e.g. 2, 3 or 4) can be used in the practical application of the present process.

In the preferred embodiments of the present invention, the peptide that is chosen to match a known amino acid sequence of a protein and to act as a protein fragment that can be liberated from the protein by a suitable treatment contains 6-30 and preferably 6-20 amino acids units.

Although the peptides chosen can be used as they are if they meet the requirements mentioned above, it is in some cases advantageous to modify them. This can be done e.g. by substitution.

Thus, while keeping the number of amino acid units the same, it is possible to substitute one or more amino acids for one or more of the amino acids present in the chosen peptide, but this substitution should preferably affect less than a quarter of the amino acids, and specifically 1, 2 or 3 of them. The new amino acid or acids thus introduced should preferably carry some free groups such as $—NH_2$, —COOH or —SH, for example.

Amongst the amino acids that can be introduced singly or multiply into the chosen peptide we may mention tyrosine and the amino acids that permit a target-oriented coupling with a carrier protein, an enzyme or any other molecule of interest.

It may also be useful to add one or more amino acids to the chosen peptide. The new amino acid or acids thus added, should advantageously be chosen among the same amino acids as for a substitution.

It may also be useful to modify the said fragment by the deletion of one or more amino acids, but this should preferably be limited to less than half of the amino acids present.

In order to prevent any interference in the identification or determination of proteins according to the present invention, the peptide can be so chosen that it has a duplicate in the amino acid sequence of a protein but does not exist as a peptide fragment in nature.

As mentioned before, the peptide can be selected for being specific either for a given protein or for a whole group or family of proteins.

In the embodiments of the process described above, the chosen peptide can be present in polymeric form, which may correspond e.g. to two protein fragments that the protein can be made to release by a suitable treatment, the fragments in question being linked via one or more disulphide bonds belonging to native cystsine units.

Polymerization can also be used to modify the immunogenic properties of one or more peptides. The polymer my consist of identical or different monomers. The monomers can be bonded together by various groups (e.g. by amino, carboxyl or sulph-hydryl groups), and especially through one or more molecules joining these monomers together.

The process described above has numerous advantages. Thus, it is no longer necessary to possess the protein as a physical entity here it is in fact enough to know from the literature the amino acid sequence or part of the amino acid sequence of the protein or proteins to be determined. The expert who is familiar with the techniques of enzymatic cleavage by one or more enzymes can predict which peptides will correspond to a fragment that the protein can be made to release by the appropriate treatment.

A peptide may be chosen either because the protein in question is the only one that contains it, or in fact for the opposite reason: because the amino acid sequence constituting it is common to a whole group or family of proteins, the aim then being to determine the entire group of proteins together.

It is also possible to choose an amino acid sequence that fulfils some special requirements, such as giving a peptide with the right size.

The selected peptide fragment can also be modified e.g. to permit:

a) coupling with a carrier protein in order to target the antigen-antibody response to a given part of the peptide fragment.

b) coupling with the molecule of interest, such as an enzyme, or c) introduction of an amino acid such as tyrosine, in order to permit labelling it with iodine-125.

The process according to the present invention also eliminates some of the drawbacks of the prior art, such as interference by other proteins. In fact, the prior art does not really offer any efficient solutions in this respect, and a great deal of preliminary work has to be done in order to find the enzymatic and/or chemical cleavage that eliminates the interfering proteins.

The expert will be able to synthesize the selected peptide by the well-known methods, such as Merrifield's solid-phase peptide synthesis.

The process according to the present invention is particularly suitable for the immunoassay of numerous protein-type hormones, which are difficult to purify and often show structural homologies. It is also suitable for the immuno-assay of viral proteins, which can otherwise be hampered by the following problems:

1) it is difficult to obtain the antigen in a sufficiently large quantity and high purity for immunizing the animals used 2) the antigens corresponding to the different strains of the same virus show great variations from strain to strain 3) the antibodies to the viral proteins present in the serum of infected individuals interfere with the analysis, and this interference can mask all or part of the epitopes recognized by the antibodies involved in the determination.

The determination of a proteolytically produced fragment solves these three problems too. Firstly, a synthetic peptide corresponding to a proteolytic fragment represents an immunogen that is very pure and available in a large quantity. Secondly, the correct choice of the amino acid sequence makes it possible to select fragments that are common to the different strains of the same virus or on the contrary are specific for one given strain. Thirdly, the epitopes of the antibodies involved in the determination which do not exist in nature cannot of course be masked by serum antibodies.

DETAILED DESCRIPTION OF THE INVENTION

Figure 1:
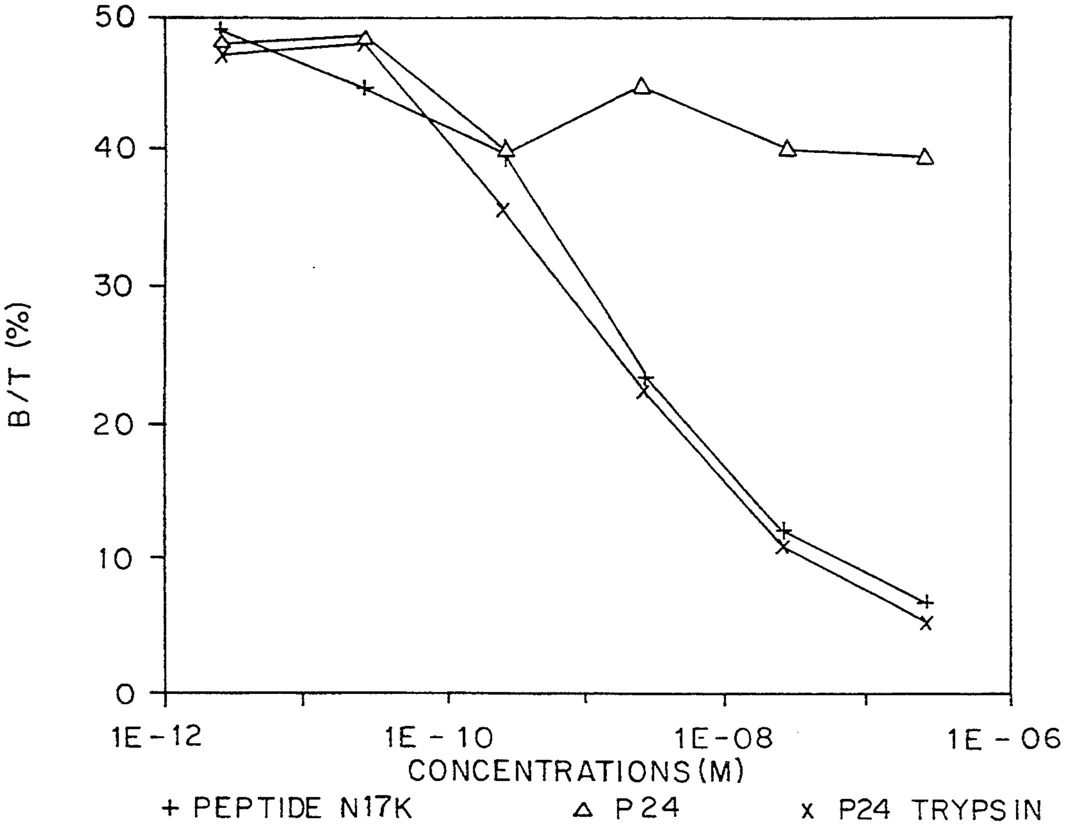
FIG. 1 shows antibody characterization using antiserum of a mouse immunized with N17K-SMCC-BJA conjugate.

The process according to the invention is further explained by the following examples, but the scope of the invention is not limited to them.

EXAMPLE 1—Determination of protein P24 of the human immunodeficiency virus (HIV)

1. Selection of the peptide fragments

Trypsin-induced fragmentation of the protein was used, because it is efficient, cheap, simple and specific, cleaving the molecule past the arginine and lysine units. The fragments obtained by digesting protein P24 of the reference strain HIV-1 BRU with trypsin were mapped on the basis of the sequence of amino acids, using the GENPRO data base and the BISANCE (CITI 2) software.

Only those trypsin-produced fragments that contained six or more amino acids were considered, These fragments were then compared with the amino acid sequences of protein P24 in the other strains of the HIV-1 and HIV-2 virus listed in the NBRF and GENPRO data bases.

Trypsin-produced fragments themselves were retained (or peptides that contained more than six amino acids and corresponded to a COOH end or an $NH_2$ end of such a fragment) if their amino acid sequence exhibited a homology of over 80% across the range of the different strains of the HIV-1 and the HIV-2 virus. These peptides were then compared with all the amino acid sequences of proteins stored in the NBRF and GENPRO data bases, but no significant homology with the amino acid sequences of other proteins was found, except for protein P24 of the HIV and SIV virus.

Four peptides (T7K, G11C, N17K and T18K) were chosen on this basis and then synthesized, these peptides being described below in turn.

1a. Identity of peptide T7K: Thr-Leu-Asn-Ala-Trp-Val-Lys (SEQ ID NO:1)

This is a complete fragment obtained by trypsin-induced cleavage and corresponding to the sequence of amino acids from No. 19 to No. 25 in protein P24 of the reference virus HIV-1 BRU. It is invariably present in all the strains of the HIV virus in which the amino acid sequence has been determined so far.

1b. Identity of peptide G11C: Gly-Ser-Asp-Ile-Ala-Gly-Thr-Thr-Ser-Thr-Cys (SEQ ID NO:2)

This peptide is formed by the sequence extending between amino acid 101 and amino acid 110 at the $NH_2$ end of the trypsin-produced fragment comprised in amino acids 101 to 131 in the reference strain of the virus, i.e. HIV-1 BRU, but an extra cysteine has been added here at the COOH end to permit chemical coupling via the SH group. This peptide is also invariably present in all the different strains of the HIV virus whose amino acid sequence has been determined so far.

1c. Identity of peptide N17K: Asn-Trp-Met-Thr-Glu-Thr-Leu-Leu-Val-Gln-Asn-Ala-Asn-Pro-Asp-Cys-Lys (SEQ ID NO:3)

This peptide is a complete fragment obtained by trypsin-induced cleavage and corresponds to the sequence between amino acid 183 and amino acid 199 in protein P24 of the reference HIV-1 strain BRU. However, the following differences can be observed among the different HIV strains:

- substitution of glutamine for glutamic acid in position 187 (for the HIV-2 ROD strain)
- substitution of glutamine for glutamic acid in position 187, substitution of serine for asparagine in position 193 and deletion of alanine in position 194 (for the HIV-2 SBLISY strain)
- substitution of glutamine for glutamic acid in position 187 and substitution of isoleucine for valine in position 191 (for the HIV-2 FG strain), and
- substitution of glycine for asparagine in position 183 (fur the HIV-1 Z2 strain).

1d. Identity of peptide T18K: Thr-Leu-Glu-Glu-Met-Met-Thr-Ala-Cys-Gln-Gly-Val-Gly-Gly-Pro-Gly-His-Lys (SEQ ID NO:4)

This peptide consists of the amino acid sequence extending from unit 210 to unit 227 at the COOH end of the trypsin-produced fragment, comprised in the section from amino acid 204 to amino acid 227 in the reference strain HIV-1 BRU. However, the following modifications can be noticed among the different HIV strains:

- substitution of leucine for methionine in position 215 and substitution of glutamine for histidine in position 226 (for the HIV-2 ROD strain)
- substitution of leucine for methionine in position 215 and substitution of isoleucine for glycine in position 220 (for the HIV-2 SBLISY strain).
- substitution of leucine for methionine in position 215, substitution of threonine for alanine in position 217 and substitution of glutamine for histidine in position 226 (for the HIV-2 FG strain), and finally
- substitution of serine for glycine in position 225 (for the HIV-1 ELI, HIV-1 MAL and HIV-1 Z2 strains).

2. Raising the antibodies

These four peptides were coupled to various carrier proteins to produce the required immunogen.

More specifically, peptide N17K was coupled with bovine serum albumin (BSA) via succinimidyl 4-(N-maleimido-methyl)cyclohexane-1-carboxylate (SMCC), which reacts both with the SH group of the native cysteine in the peptide and with the $\epsilon$-$NH_2$ groups of the lysine units in the carrier protein.

The bovine serum albumin from Serva was dissolved in a 0.1M phosphate buffer (pH 7) to a concentration of 5 mg/ml. The SMCC reagent from Pierce was dissolved in dimethylformamide (DMF) to a concentration of 25 mg/ml, and the solution obtained was added to the BSA solution in a molar ratio of 1:50.

After incubation for 1 h at room temperature, the various reagents were separated by passage through a molecular sieve in the form of a Biogel P2 column from Bio-Rad, which had been equilibrated with a 0.1M phosphate buffer (pH 6).

The peptide was then introduced into the BSA-SMCC solution in a molar ratio of 30:1, and the reaction mixture was incubated for 12 h at 4° C.

The immunogen thus obtained was purified by passing the reaction mixture through a molecular sieve in the form of a Biogel P4 column from Bio-Rad, which had been equilibrated with phosphate-buffered saline (PBS; pH 7.2).

Four BALB/c mice were inoculated at monthly intervals with 50 μg of this immunogen, incorporated in Freund's complete adjuvant, half the injections being given subcutaneously and the other half intraperitoneally.

3. Characterization of the antibodies

The antibodies thus obtained were characterized by making use of their ability to bind a radioactive tracer, which consisted here of the peptide N17K, coupled with glycyl-L-tyrosine (GT), isotopically labelled with iodine-125.

A 20-mmole solution of glycyl-L-tyrosine (GT) from Sigma in a 0.1M phosphate buffer (pH 7.0) was first prepared, and a 25-mg/ml solution of SMCC from Pierce in dimethylformamide (DMF) was added to it in a molar ratio of 1:1. The reaction mixture thus obtained was incubated at 20° C. for 2 h.

The GT-SMCC conjugate formed was purified by reverse-phase high-pressure liquid chromatography (HPLC), and then coupled with the peptide N17K, used in a 0.5-mmole solution in 0.1M phosphate buffer (pH 6.0), the molar ratio between them being 1:1.

After incubation at 4° C. for 12 h, the resulting N17K-SMCC-GT was purified by reverse phase HPLC. The resulting N17K-SMCC-GT tracer system was labelled with iodine-125 by the chloramine T method and purified again by high-pressure liquid chromatography.

FIG. 1 shows the results obtained with the antiserum of a mouse immunized with the N17K-SMCC-BSA conjugate. More specifically, this diagram was obtained as follows. 100 μl of the mouse antiserum was diluted 1:1000 with the 0.1% BSA-PBS buffer mixture (pH 7.2). To this dilution were added 50 μl of the isotopically labelled N17K-SMCC-GT tracer in the same buffer, together with:

- 50 μl of peptide N17K in one case,
- 50 μl of protein P24 of the HIV-1 BRU strain (ex Transgene) in another case, and
- 50 μl of protein P24 that had been treated with trypsin in the third case, these constituents being added at different concentrations in ordinary human plasma.

The mixtures were incubated at 4° C. for 12 h, and the resulting antigen-antibody complexes were precipitated by the addition of 200 μl of an aqueous 20% solution of polyethylene glycol with an average molecular weight of 6000 (PEG 6000), followed by centrifuging. The radioactivity of the sediment formed was finally measured. As FIG. 1 shows, the antibodies recognized both peptide N17K and protein P25 treated with trypsin, but they did not respond to native protein P24.

The quantitative determination of peptide N17K therefore clearly permits the determination of protein P24 of the HIV-1 BRU strain, but it should also permit the determination of protein P24 in all the other strains of the HIV virus that exhibit a structural homology with this fragment.

EXAMPLE 2—Determination of the lipotropic pituitary hormone (LPH)

A method was developed for the immunoassay of the lipotropic pituitary hormone with the aid of antibodies raised to the $NH_2$-terminal hexapeptide (E6R) Glu-Leu-Thr-Gly-Gln-Arg (SEQ ID NO:5). This peptide corresponds to a trypsin-produced fragment but does not show any significant homology with any of the amino acid sequences of proteins listed in the NBRF and GENPRO data bases.

In order to produce antibodies directed specifically against the COOH and $NH_2$ ends of this fragment, the animals were immunized with a peptide having the amino acid sequence Glu-Leu-Thr-Cys-Gln-Arg (SEQ ID NO:6), where a glycine unit that had been present in the original fragment was replaced by a cystsine unit, in order to make it possible to couple this peptide to a carrier protein via the SH group of cysteine.

Succinimidyl 4-(N-maleimidomethyl)cyclohexane-1-carboxylate (SMCC) was again used to bring about this coupling, as it reacts both with the SH group of the native or added cystsine unit of the peptide and with the $\epsilon$-$NH_2$ groups of the lysine units present in the carrier protein.

Bovine serum albumin (BSA) from Serva was dissolved in a 0.1M (phosphate buffer (pH 7) to a concentration of 5 mg/ml. The SMCC reagent from Pierce was dissolved in dimethylformamide (DMF) to a concentration of 25 mg/ml, and the SMCC solution was added to the BSA solution in a molar ratio of 1:50.

After incubation for 1 h at room temperature, the various reagents were separated by passage through a molecular sieve in the form of a Biogel P2 column from Bio-Rad, which had been equilibrated with a 0.1M phosphate buffer (pH 6).

The peptide was then introduced into the BSA-SMCC solution in a molar ratio of 30:1, and the reaction mixture was incubated for 12 h at 4° C.

The immunogen formed was purified by passing the reaction mixture through a molecular sieve in the form of a Biogel P4 column from Bio-Rad, which had been equilibrated with phosphate-buffered saline (PBS; pH 7.2).

Eight BALB/c mice and two rabbits were inoculated at monthly intervals by the subcutaneous injection of respectively 50 and 250 μg of this immunogen, incorporated in Freund's complete adjuvant. Two of these animals produced antibodies that could be used to determine the lipotropic pituitary hormone.

Figure 2:
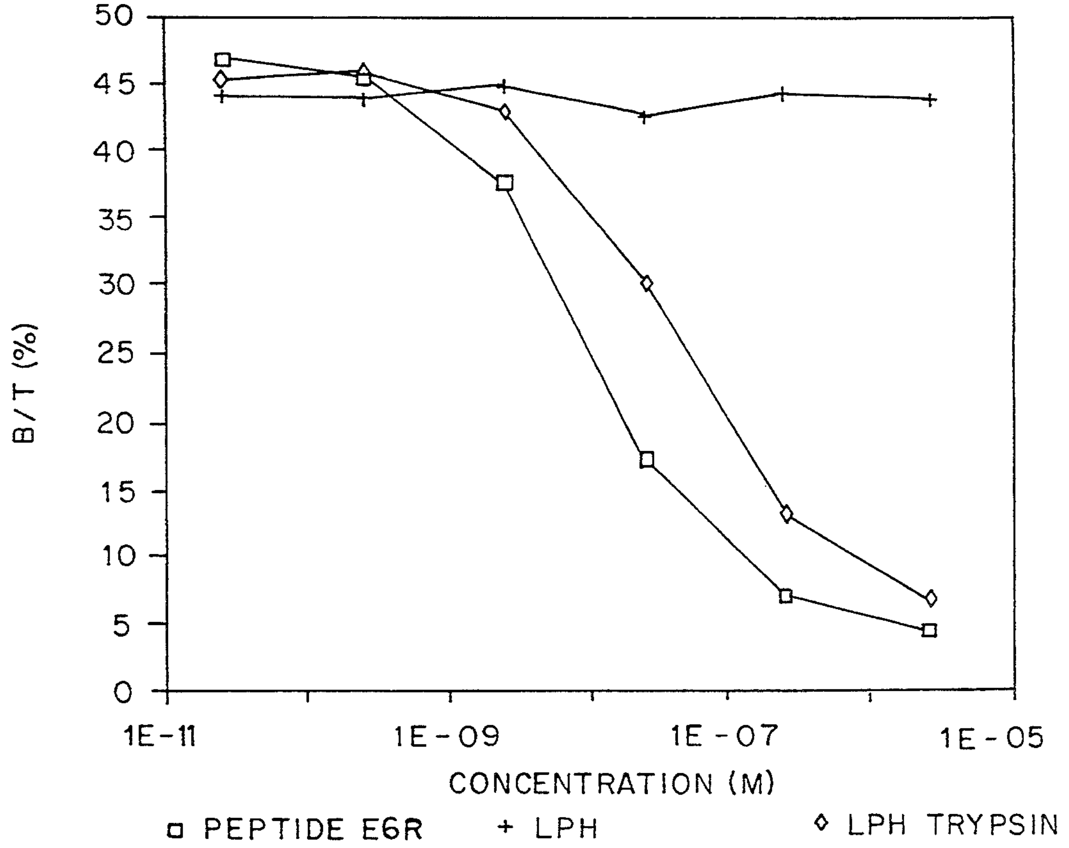
FIG. 2 shows determination of LPH using antibodies raised to the $NH_2$-terminal hexapeptide Glu-Leu-Thr-Glu-Gln-Arg.

The serum sample was treated with trypsin to effect the release of the $NH_2$-terminal peptide, and the determination was carried out on the basis of competition between this and an identical peptide coupled to glycyl-L-tyrosine (GT) with the aid of SMCC, where GT was again labelled with radio-active iodine-125. The results of the immunoassay are shown in FIG. 2.

This example shows that the process according to the present invention can be used for the immunoassay of the lipotropic pituitary hormone, for which it is particularly difficult to obtain a large enough quantity of suitably pure protein for immunization.

We claim:

1. In a process for assaying a known protein comprising a particular natural peptide by preparing a synthetic peptide, preparing antibodies against said synthetic peptide, and assaying said protein with said antibodies, the improvement consisting essentially of:

(a) selecting from the known amino acid sequence of said protein a natural peptide corresponding to a fragment which can be obtained by non-endogenous enzymatic treatment of said protein, which natural peptide is representative of said protein or a group of proteins;

(b) preparing a synthetic peptide corresponding to said natural peptide;

(c) preparing antibodies against said synthetic peptide;

(d) assaying a sample for said protein comprising;

(e) treating said sample to cleave said protein at a first enzymatic proteolytic site using a first proteolytic enzyme and at a second enzymatic proteolytic site using a second proteolytic enzyme to obtain a natural peptide of from 6 to 30 amino acids, said first proteolytic enzyme and said second proteolytic enzyme being the same or different; and (f) immunologically determining the amount of said second natural peptide by reacting said second natural peptide with said antibodies;

(g) calculating the amount of protein in said sample, whereby the amount of the protein is determined as a known proportion of said second natural peptide.

2. The process according to claim 1 wherein said known sequence has from 6 to 30 amino acids and said second natural peptide has from 6 to 30 amino acids.

3. Process as in claim 1, wherein the synthetic peptide contains 6-20 amino acids.

4. The process according to claim 1 wherein the protein is assayed qualitatively.

5. The process according to claim 1 wherein the protein is assayed quantitatively.

6. The process of claim 1 wherein the synthetic peptide contains at least one specific epitope of said first natural peptide.

7. Process according to claim 1 wherein the synthetic peptide corresponds to the C-terminal or the N-terminal part of the natural peptide.

8. Process as in claim 1, wherein characterized in that the peptide chosen has a duplicate in the synthetic amino acid sequence of a protein but does not exist in nature in the form of a fragment.

9. Process as in claim 1, wherein characterized in that the synthetic peptide is chosen for its specificity for a single protein.

10. Process as in claim 1, wherein characterized in that the synthetic peptide is chosen for its specificity for a family of proteins.

11. Process as in claim 1, wherein characterized in that the synthetic peptide is used in polymeric form.

12. The process according to claim 1 wherein the protein is LPH.

13. The process according to claim 1 wherein the protein is p24 of the HIV virus.

14. The method according to claim 1 wherein the known protein is P24 protein of HIV, the first synthetic peptide is Gly-Ser-Asp-Ile-Ala-Gly-Thr-Thr-Ser-Thr-Cys; and said first proteolytic enzyme and said second proteolytic enzyme are trypsin.

15. The method according to claim 1 wherein the known protein is P24 protein of HIV, the first natural peptide is Asn-Trp-Met-Thr-Glu-Thr-Leu-Leu-Val-Gln-Asn-Ala-Asn-Pro-Asp-Cys-Lys; and said first proteolytic enzyme and said second proteolytic enzyme are trypsin.

16. The method according to claim 1 wherein the known protein is P24 protein of HIV, the first synthetic peptide is Thr-Leu-Glu-Glu-Met-Met-Thr-Ala-Cys-Gln-Gly-Val-Gly-Gly-Pro-Gly-His-Lys; and said first proteolytic enzyme and said second proteolytic enzyme are trypsin.

17. A process for assaying a sample containing a family of known proteins which include a common natural peptide comprising:

(a) selecting from the known amino acid sequence of said family of proteins a natural peptide corresponding to a fragment which can be obtained by non-endogenous enzymatic treatment of each member of-said family of proteins, which natural peptide is representative of said family of proteins;

(b) preparing a synthetic peptide corresponding to said natural peptide;

(c) preparing antibodies against said synthetic peptide;

(d) assaying a sample for said protein comprising:

(e) treating said sample with a first proteolytic enzyme to cleave said family of proteins at said first enzymatic proteolytic site and treating said sample with a second proteolytic enzyme to cleave said family of proteins at said second enzymatic proteolytic site, said first proteolytic enzyme and said second proteolytic enzyme being the same or different;

(f) immunologically determining the amount of said natural peptide by reacting said natural peptide with said antibodies; and (g) calculating the amount of family of proteins in said sample, whereby the amount of the family of proteins is determined as a known proportion of said second natural peptide.

18. A process according to claim 17 wherein the synthetic peptide contains from 6-30 amino acids.

19. A process according to claim 17 wherein the synthetic peptide contains from 6-20 amino acids.

20. A process according to claim 17 wherein the family of proteins is assayed qualitatively.

21. A process according to claim 17 wherein the family of proteins is assayed quantitatively.

22. A process according to claim 17 wherein the synthetic peptide contains at least one specific epitope of said first natural peptide.

23. A process according to claim 17 wherein the synthetic peptide corresponds to the C-terminal or the N-terminal part of the natural peptide.

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
( A ) LENGTH: 7 amino acids
( B ) TYPE: amino acid
( D ) TOPOLOGY: linear ( i i ) MOLECULE TYPE: peptide ( x i ) SEQUENCE DESCRIPTION: SEQ ID NO:1:

```
Thr Leu Asn Ala Trp Val Lys
1               5
```

( 2 ) INFORMATION FOR SEQ ID NO:2:

( i ) SEQUENCE CHARACTERISTICS:
( A ) LENGTH: 11 amino acids
( B ) TYPE: amino acid
( D ) TOPOLOGY: linear ( i i ) MOLECULE TYPE: peptide ( x i ) SEQUENCE DESCRIPTION: SEQ ID NO:2:

```
Gly Ser Asp Ile Ala Gly Thr Thr Ser Thr Cys
1               5                   10
```

( 2 ) INFORMATION FOR SEQ ID NO:3:

( i ) SEQUENCE CHARACTERISTICS:
( A ) LENGTH: 17 amino acids
( B ) TYPE: amino acid
( D ) TOPOLOGY: linear ( i i ) MOLECULE TYPE: peptide ( x i ) SEQUENCE DESCRIPTION: SEQ ID NO:3:

```
Asn Trp Met Thr Glu Thr Leu Leu Val Gln Asn Ala Asn
1               5                   10

Pro Asp Cys Lys
    15
```

( 2 ) INFORMATION FOR SEQ ID NO:4:

( i ) SEQUENCE CHARACTERISTICS:
( A ) LENGTH: 18 amino acids
( B ) TYPE: amino acid
( D ) TOPOLOGY: linear ( i i ) MOLECULE TYPE: peptide ( x i ) SEQUENCE DESCRIPTION: SEQ ID NO:4:

```
Thr Leu Glu Glu Met Met Thr Ala Cys Gln Gly Val Gly
1               5                   10

Gly Pro Gly His Lys
    15
```

( 2 ) INFORMATION FOR SEQ ID NO:5:

( i ) SEQUENCE CHARACTERISTICS:
( A ) LENGTH: 6 amino acids
( B ) TYPE: amino acid
( C ) TOPOLOGY: linear ( i i ) MOLECULE TYPE: peptide ( x i ) SEQUENCE DESCRIPTION: SEQ ID NO: 5:

```
Glu Leu Thr Gly Gln Arg
1               5
```

-continued ( 2 ) INFORMATION FOR SEQ ID NO:6:

( i ) SEQUENCE CHARACTERISTICS:
( A ) LENGTH: 6 amino acids
( B ) TYPE: amino acid
( C ) TOPOLOGY: linear ( i i ) MOLECULE TYPE: peptide ( x i ) SEQUENCE DESCRIPTION: SEQ ID NO: 6:

Glu Leu Thr Cys Gln Arg
1 5